Feb. 7, 1961 G. J. VON ABRAMS Plant Pat. 2,020
ROSE PLANT
Filed Feb. 26, 1960
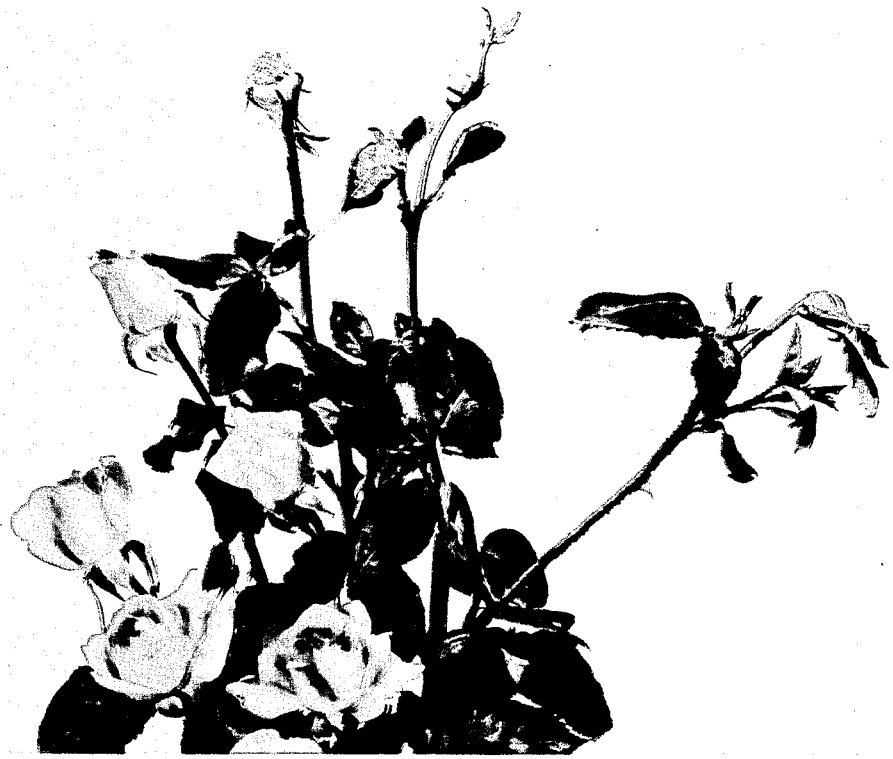
Inventor
Gordon J. Von Abrams
by F. R. Geiler.
Attorney United States Patent Office Plant Pat. 2,020

Patented Feb. 7, 1961

2,020

ROSE PLANT

Gordon J. Von Abrams, Portland, Oreg., assignor to Eldon Pinkeney Dering, Scappoose, Oreg.

Filed Feb. 26, 1960, Ser. No. 11,392

1 Claim. (Cl. 47—61)

This invention comprises a new and distinct variety of rose plant of the "hybrid tea" class, the novel and distinguishing characteristics of which are particularly the unique flower color, the high-centered flower form and size, the contrasting dark color of the foliage, and the bushy upright growth of the plant.

This new rose plant resulted from pollinating the rose variety "Sutter's Gold" (Plant Patent No. 885) with the pollen of an unnamed variety which I had previously originated by crossing the variety "Mme. Henri Guillot" (Plant Patent No. 337) with the variety "PD No. 5023–23" (unpatented and not in commerce). One of my objects in originating the present rose plant was to produce a rose of a unique color. The pollinating took place in 1951 at Scappoose, Oregon, the first flower was produced in 1952, and the plant was first asexually reproduced at Scappoose, Oregon, in 1952, by bud-grafting. Since then the variety has retained its distinguishing characteristics through succeeding propagations by bud-grafting.

The flower color of the new variety is less yellow than that of the seed parent ("Sutter's Gold") and the plant is less tall in habit.

In comparison with the pollen parent ("Mme. Henri Guillot" crossed with "PD 5023–23") the new variety is more yellow in flower color, has more petals, is shorter and more compact in plant habit, and somewhat less vigorous in growth and less resistant to disease.

The new variety is somewhat similar in color and in general habit to the variety "Mojave" (Plant Patent No. 1,176) but the flower color of the new variety is more yellow and less red, particularly at the base of the petals (outer surface); the flower color does not fade as quickly and remains more intense and less pale in senescence than that of the "Mojave"; also the flower generally has more petals and the plant has more large thorns and is slightly more vigorous in growth than the "Mojave."

The accompanying illustration shows the plant in color with separated blooms in different stages of development. A detailed description follows in which the following standard references for color are cited:

(1) Wilson, R. F.; Royal Horticultural Society Colour Chart, England, 1940.

(2) Ridgway, R.; Color Standards and Color Nomenclature, Washington, D.C., 1912.

(3) Nickerson Color Fan, Munsell Color Co., Baltimore, 1957.

*Flowers*

The flowers are borne singly on long stems, or frequently in cymes of three to seven flowers, on medium stems.

The plant blooms abundantly outdoors and blooms almost continuously outdoors during the growing season.

The flowers have a light fruity fragrance.

Longevity: Plant outdoors in September, 5 days; cut flowers from outdoor plant in September, 3 days. Petals drop cleanly.

Flower color (of newly opened flowers, grown outdoors at Scappoose, Oregon, blooming in September 1959): General color effect (face on)—near Mandarin Red (Wilson, 17, page 17).

*Outside petal.*—Outer surface—basal fan near Canary Yellow (Wilson 2/1, p. 2, to 2/2, p. 2) extending upward about ⅓ the length of the petal, merging irregularly with various shades and tints of red, from near Indian Orange (Wilson, 713, p. 155) to near Dutch Vermilion (Wilson, 717, p. 156), sometimes with areas flushed as deep red as Turkey Red (Wilson, 721, p. 94). The main "veins" of the petal show clearly, being darker and more red (i.e.—Turkey Red (Wilson 721) than the surrounding tissue. Inner surface—basal fan near Buttercup Yellow (Wilson, 5, p. 5) extending upward ca. one third or less, the length of the petal, and merging quite sharply with the predominant color, a very intense, almost luminescent, orange-red, between Dutch Vermilion (Wilson, 717, p. 156) and Orient Red (Wilson, 819, p. 165).

*Intermediate petal.*—Outer surface—basal fan near Canary Yellow (Wilson, 2/1, p. 2) extending upward ⅓ or more than ⅓ the length of the petal, merging gradually with near Poppy Red (Wilson, 16 to 16/1, p. 16). Toward the lateral margins, the color is darker and more intense, near Dutch Vermilion (Wilson, 717, p. 156). "Veins" slightly darker. Inner surface—basal fan near Lemon Yellow (Wilson, 4, p. 4) extending upward ca. ⅓ or less than ⅓ the length of the petal, and merging quite sharply with from Mandarin Red (Wilson, 17 to 17/1, p. 17) to Dutch Vermilion (Wilson, 717, p. 156) or even a deeper shade of this hue. "Veins" very slightly darker, not obvious.

*Inside petal.*—Outer surface—basal fan near Canary Yellow (Wilson 2, to 2/1, p. 2) extending upward ⅓ or more than ⅓ the length of the petal, merging gradually and often irregularly with near Mandarin Red (Wilson, 17/1, p. 17). "Veins" darker. Inner surface—basal fan near Lemon Yellow (Wilson, 4, p. 4) extending upward about ¼ the length of the petal, merging sharply with from near Mandarin Red (Wilson, 17, p. 17) to near Dutch Vermilion (Wilson, 717, p. 156).

Flower color (of flowers three days after opening in September 1959, at Scappoose, Oregon): General color effect (face on)—near Azalea Pink (Wilson, 618, p. 74), sometimes more blue, i.e., Porcelain Rose (Wilson 620, p. 147) with yellow overtones. Under conditions of high temperature and high light intensity the color becomes less yellow and of lighter tone, the general effect being a more blue appearance.

*Outside petal.*—Outer surface—basal fan near Canary Yellow (Wilson, 2 to 2/1, p. 2) extend upward ⅓ or more than ⅓ the length of the petal, merging gradually with Mandarin Red (Wilson, 17/1 to 17/2, p. 17). Sometimes irregularly marked or flushed with a bluer red of darker shade, particularly along the "veins," i.e. near Carmine (Wilson, 21, p. 21). Inner surface—basal fan near Aureolin (Wilson, 3, p. 3) extending upward ca. ⅓ the length of the petal, blending gradually through intermediate orange hues to the predominant color, between Geranium Lake (Wilson, 20/1, p. 20) and Carmine (Wilson, 21/1, p. 21).

*Intermediate petal.*—Outer surface—basal fan near Canary Yellow (Wilson, 2/1, p. 2) extending upward ⅓ or more than ⅓ the length of the petal, blending gradually into near Mandarin Red (Wilson, 17/2, p. 17). Inner surface—basal fan near Aureolin (Wilson, 3, p. 3) extending upward less than ⅓ the length of the petal, blending rather shortly through intermediate orange colors to near Vermilion (Wilson, 18/1 to 18/2, p. 18). Sometimes more blue, i.e., near Geranium Lake (Wilson, 20/2, p. 20). "Veins" slightly darker.

*Inside petal.*—As intermediate petal.

Size and form of open flower:

*Size.*—Large (for example, 13 cm. in diameter).

*Form.*—High-centered, remaining so well into maturity when a gradual flattening occurs. The petals at first are slightly but firmly cupped inwardly, becoming flatter at maturity, and slightly rolled outwardly at apex. The petals (petaloids) of the innermost row of petals tend to be irregular and rough in outline.

*Petalage.*—Double, 28–35 petals.

Further flower details:

*Petals.*—Substance—medium thick, crisp. Texture: Inner surface—satiny; outer surface—satiny. Shape: Outside petal—broadly obovate (i.e., 6 cm. wide x 6.5 cm. long). Apical margin irregular. Intermediate petal—obovate (i.e., 5 cm. wide x 6.2 cm. long). Apical margin irregular. Inside petal—obovate (i.e., 4.5 cm. wide x 6.0 cm. long). Apical margin irregular. The innermost row is often constituted of very irregular petaloids.

*Sepals.*—Size—medium (i.e., 1.0 x 4.2 cm., including terminal foliaceous appendages). Shape—spear shaped; curled back to peduncle. Foliaceous appendages typically present, both lateral and terminal. Color: Outer surface—no close match. Between Scheele's Green (Ridgway, 33, GY–G. *i*, Plate VI) and Peacock Green (Ridgway, 35, GREEN. *i*, Plate VI) irregularly flushed reddish. Inner surface—pubescent. Near Corydalis Green (Ridgway, 29‴, GG–Y. *d*, Plate XLI). Irregularly flushed reddish.

Flower bud:

*Peduncle.*—Medium length (i.e., 6 cm.); medium caliber (3–4 mm.); erect. Color near Scheeles Green (Wilson, 860/2, p. 175) usually with slight reddish flush on one side. Few glandular cilia, several very small reddish thorns.

*Before calyx breaks.*—Size—medium large (i.e., 1.9 cm. x 3.5 cm., including calyx-tube but excluding terminal foliaceous appendages). Form—medium-long pointed, with ordinary calyx-tube; with foliaceous appendages on one or both lateral margins of most sepals, but usually with none on two of the five sepals, with moderately-incised terminal foliaceous appendages extending beyond the tip of the bud, usually ca. ⅓ the length of the bud. Color—near Scheele's Green (Wilson, 860, p. 175).

*As calyx breaks.*—Color near Orange Rufous (Ridgway, II Orange *i*, Plate II) irregularly flushed near Blood Red (Wilson, 820/3, p. 166).

*As first petal opens.*—Size—medium large (i.e., 2.5 x 4.0 cm.). Form—long pointed. Color: Outer surface—near Mandarin Red (Wilson, 17, p. 17) flushed irregularly upward from base with near Lemon Yellow (Wilson, 4, p. 4). "Veins" strongly marked and petal irregularly flushed with Orient Red (Wilson, 819, p. 165). Inner surface—brighter than Orient Red (Wilson, 819, p. 165). Base Lemon Yellow (Wilson, 4, p. 4).

*Opening habit.*—Opens very well.

Plant foliage:

*Leaf.*—Compound, 5 to 7 leaflets, usually 5; moderately abundant.

*Leaflets.*—Size—large (i.e., 4.2 x 7.5 cm.). Substance—medium thick; hard. Texture—glossy.

Shape—ovate; with apex acute, base rounded; margin singly or irregularly serrate. Color: Mature—upper surface—no good match; related to Dark Dull Yellow-Green (Ridgway, 31″, Y–G. *m*, Plate XXXII); under surface—between Asphodel Green (Ridgway 29‴, GG–Y., Plate XLI) and Pois Green (Ridgway, 29‴, GG–Y. *i*, Plate XLI). Young—upper surface—no close match; possibly related to Fern Green (Wilson, 0862, p. 186) but much darkened by the presence of anthocyanin pigments; under surface—no match; related to Mineral Red (Ridgway, 1″, RED *k*, Plate XXVII), with green undertone. (The interplay here of red and green in a fairly translucent tissue makes comparison extremely difficult.)

*Rachis.*—Medium. Upper side—groove narrow but not shallow. Margins of groove with several gland-tipped cilia, few prickles. Under side—quite smooth, with few relatively heavy thorns. In the immature rachis, the groove, and upper surfaces, are pubescent.

*Stipules.*—Size medium (i.e., 0.8 x 2.5 cm.). Points medium (i.e., 5 mm.), turning out at an angle of less than 90°.

Plant stems and branches:

*Main stems (of current year's growth).*—Dull gray-green. Thorns—several; medium long (i.e. 12 mm.); hooked slightly downward; with medium oval base (i.e. 5 mm. x 13 mm.); dark brown.

*Branches (currently bearing senescent flowers).*—Dull gray-green. Thorns—several to numerous; medium long (i.e., 11 mm.); hooked moderately downward; with medium oval base (i.e. 3 mm. x 10 mm.) light tan with reddish flush.

*New shoots (in rapid growth).*—Green flushed red, near Garnet Brown (Wilson, 00918/1, p. 192). Thorns—several; medium long (i.e., 10 mm.) hooked slightly downward; with medium oval base (i.e. 2 mm. x 9 mm.).

Further plant characteristics: The plant is bushy, upright, medium tall (up to 4 feet or more), moderately branched, and grows freely.

Reproductive organs:

*Stamens.*—Moderate number, arranged quite regularly about pistils, on outer margin of calyx-tube disc, immediately adjacent to petals. Filaments—medium length (i.e., 13 mm.). Nearly all with anthers. Red at base, yellow above. Anthers—size medium (i.e., 1 x 4 mm.); color, orange. Pollen—abundant and viable.

*Pistils.*—Numerous. Styles—contorted, slightly uneven in length. Caliber medium; length medium (i.e., 7 mm.). Loosely bunched, free. Stigma—ordinary; yellowish. Ovaries—several exposed above calyx-tube, surrounded by cottony tissue.

*Receptacle.*—Shape—depressed, turbinate, near conical. Rim (disc) prominent. Size—small (i.e., 9 mm. high x 13 mm. in diameter). Surface—very lightly pubescent. Color—near Scheele's Green (Ridgway, 33 GY–G. *i*, Plate VI).

*Fruit ("seed pod").*—Near globular (i.e. 2 cm. high x 2.5 cm. diameter), slightly compressed; without conspicuous "neck"; mature color deep orange to red, variable with age and environment. Wall fleshy, medium thick (i.e. 4 mm.).

*Sepals.*—Usually persistent.

*Seed.*—Many; medium large; most are viable.

Having thus disclosed my invention, I claim:

A new and distinct variety of rose plant of the "hybrid tea" class characterized particularly by its unique flower color, the large size and high-centered form of the flower in full bloom, the contrasting dark color of the foliage, and the bushy upright growth of the plant.

No references cited.